United States Patent
Ando et al.

(10) Patent No.: US 11,782,426 B2
(45) Date of Patent: Oct. 10, 2023

(54) ABNORMALITY SCORE CALCULATION APPARATUS, METHOD, AND MEDIUM

(71) Applicant: KABUSHIKI KAISHA TOSHIBA, Tokyo (JP)

(72) Inventors: Jumpei Ando, Yokohama (JP); Wataru Watanabe, Tokyo (JP); Takayuki Itoh, Kawasaki (JP); Toshiyuki Ono, Kawasaki (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 260 days.

(21) Appl. No.: 17/186,656

(22) Filed: Feb. 26, 2021

(65) Prior Publication Data

US 2022/0083033 A1 Mar. 17, 2022

(30) Foreign Application Priority Data

Sep. 16, 2020 (JP) ................................ 2020-155587

(51) Int. Cl.
  *G05B 19/418* (2006.01)
  *G01N 33/00* (2006.01)
  *G06F 16/28* (2019.01)
(52) U.S. Cl.
  CPC ....... *G05B 19/41875* (2013.01); *G01N 33/00* (2013.01); *G06F 16/285* (2019.01); *G01N 2033/0078* (2013.01); *G05B 2219/34475* (2013.01)
(58) Field of Classification Search
  CPC ............................. G01N 33/00; G06T 11/206
  See application file for complete search history.

(56) References Cited

U.S. PATENT DOCUMENTS

| 10,521,193 | B2 | 12/2019 | Tasaki |
| 10,977,568 | B2* | 4/2021 | Shibuya ................. G06N 20/00 |
| 11,436,769 | B2* | 9/2022 | Watanabe ............... G06T 11/60 |
| 2020/0149998 | A1* | 5/2020 | Ayyagari ........... G05B 23/0237 |

(Continued)

FOREIGN PATENT DOCUMENTS

| JP | 2009-076056 A | 4/2009 |
| JP | 2021-71896 A | 5/2021 |

(Continued)

OTHER PUBLICATIONS

Industrial AI/IoT EXPO Report, Toshiba Digital Solutions Corporation, https://www.toshiba-sol.co.jp/industry/meister/contents/img/event202001/panel-p-budomari.pdf, accessed Feb. 10, 2021, 2 pages (with English translation).

*Primary Examiner* — Bryan Bui
(74) *Attorney, Agent, or Firm* — Oblon, McClelland, Maier & Neustadt, L.L.P.

(57) ABSTRACT

An abnormality score calculation apparatus according to an embodiment includes a processing circuit configured to: acquire first data concerning a status of a product or a manufacturing process; calculate based on the first data an abnormality score for a respective one of a plurality of abnormality modes or for a respective one of a plurality of pieces of the first data of various types; and convert a scale of a respective one of a plurality of abnormality scores including the abnormality score in such a manner that the abnormality scores become substantially equal in occurrence degree.

14 Claims, 7 Drawing Sheets

(56) References Cited

U.S. PATENT DOCUMENTS

2021/0134032 A1    5/2021  Watanabe et al.
2021/0150640 A1*   5/2021  Tanaka ............. G06Q 10/06393
2022/0188307 A1    6/2022  Watanabe et al.

FOREIGN PATENT DOCUMENTS

JP            2022-92419 A      6/2022
WO       WO 2015/118946 A1      8/2015

* cited by examiner

F I G. 1

| ID | Data 1 | Data 2 | Data 3 | Data 4 | ... | Data N-1 | Data N |
|---|---|---|---|---|---|---|---|
| XXXX-000001 | 0.013782348 | 1208.47 | 7071 | 1 | ... | A | 2020/9/1 7:23 PM |
| XXXX-000002 | 0.204271253 | 1042.27 | 7079 | 1 | ... | A | 2020/9/1 7:23 PM |
| XXXX-000003 | 0.43908569 | 1067.70 | 7121 | 1 | ... | B | 2020/9/1 7:24 PM |
| XXXX-000004 | 0.903287843 | 1013.33 | 7794 | 1 | ... | C | 2020/9/1 7:24 PM |
| XXXX-000005 | 0.127749749 | 1247.24 | 7181 | 1 | ... | A | 2020/9/1 7:25 PM |
| XXXX-000006 | 0.085181038 | 1049.24 | 7702 | 1 | ... | C | 2020/9/1 7:27 PM |
| XXXX-000007 | 0.245164501 | 1024.45 | 7487 | 1 | ... | B | 2020/9/1 7:27 PM |
| ... | ... | ... | ... | ... | ... | ... | ... |
| XXXX-010009 | 0.608148803 | 1194.97 | 7465 | 2 | ... | C | 2020/9/2 8:05 AM |
| XXXX-010010 | 0.469019611 | 1042.20 | 7788 | 2 | ... | A | 2020/9/3 8:06 AM |
| XXXX-010011 | 0.432882553 | 1029.57 | 7474 | 2 | ... | A | 2020/9/4 8:07 AM |
| XXXX-010012 | 0.209109323 | 1078.67 | 7602 | 2 | ... | B | 2020/9/5 8:07 AM |
| XXXX-010013 | 0.919125396 | 1210.83 | 7714 | 2 | ... | A | 2020/9/6 8:08 AM |
| XXXX-010014 | 0.335275839 | 1032.62 | 7993 | 2 | ... | A | 2020/9/7 8:08 AM |
| XXXX-010015 | 0.350644304 | 1167.72 | 7094 | 2 | ... | C | 2020/9/8 8:09 AM |
| XXXX-010016 | 0.453598245 | 1023.28 | 7519 | 2 | ... | B | 2020/9/9 8:10 AM |
| XXXX-010017 | 0.195686009 | 1151.77 | 7303 | 2 | ... | A | 2020/9/10 8:15 AM |

FIG. 2

| Manufacturing management unit | Data 1 | Data 2 | Data 3 | ... | Data N-1 | Data N |
|---|---|---|---|---|---|---|
| 1 | 0.109497 | 0.402525 | 0.56402 | ... | 0.808817 | 0.364191 |
| 1 | 0.965166 | 0.202206 | 0.195305 | ... | 0.889133 | 0.061792 |
| 1 | 0.460044 | 0.309382 | 0.681455 | ... | 0.209095 | 0.472755 |
| ... | ... | ... | ... | ... | ... | ... |
| 2 | 0.558338 | 0.70533 | 0.745689 | ... | 0.653061 | 0.20242 |
| 2 | 0.428765 | 0.048491 | 0.942074 | ... | 0.390718 | 0.985581 |
| 2 | 0.830002 | 0.876185 | 0.532414 | ... | 0.743864 | 0.815183 |
| 2 | 0.59793 | 0.093462 | 0.997238 | ... | 0.19006 | 0.838313 |
| ... | ... | ... | ... | ... | ... | ... |
| N | 0.698152 | 0.443079 | 0.475949 | ... | 0.506611 | 0.927288 |
| N | 0.226827 | 0.652228 | 0.164287 | ... | 0.898019 | 0.749549 |
| N | 0.080476 | 0.430625 | 0.879703 | ... | 0.163264 | 0.763448 |
| N | 0.935547 | 0.998463 | 0.632722 | ... | 0.48557 | 0.696504 |

FIG. 3

| Feature quantity name | First sub-data (first range) | Second sub-data (second range) |
|---|---|---|
| Average | 0.47 | 0.51 |
| Variance | 0.2 | 0.23 |
| Median | 0.48 | 0.51 |
| Maximum value | 0.98 | 0.98 |
| Minimum value | 0.01 | 0.02 |
| Q3 | 0.71 | 0.74 |
| Q1 | 0.13 | 0.15 |
| Number of pieces of data | 3000 | 2800 |
| ... | ... | ... |

| Abnormality ranking | |
|---|---|
| First place: Abnormality mode 1: Data 4 | Abnormality score 0.94 |
| Second place: Abnormality mode 3: Data 1 | Abnormality score 0.87 |
| Third place: Abnormality mode 2: Data 2 | Abnormality score 0.73 |
| ⋮ | |
| N place: Abnormality mode 4: Data 3 | Abnormality score 0.00 |

FIG. 9

| Abnormality mode 1 | Abnormality mode 2 | ⋯ | Abnormality mode M |

Abnormality ranking

| First place: Data 4 | Abnormality score 0.94 |
| Second place: Data 1 | Abnormality score 0.87 |
| Third place: Data 2 | Abnormality score 0.73 |

⋮

| N place: Data 3 | Abnormality score 0.00 |

F I G. 10

Timeline

June 12

| First place: Abnormality mode 1: Data 4 | Abnormality score 0.94 |
| Second place: Abnormality mode 3: Data 1 | Abnormality score 0.87 |
| Third place: Abnormality mode 2: Data 2 | Abnormality score 0.73 |

June 11

| First place: Abnormality mode 4: Data 2 | Abnormality score 0.94 |
| Second place: Abnormality mode 1: Data 1 | Abnormality score 0.87 |
| Third place: Abnormality mode 3: Data 2 | Abnormality score 0.73 |

F I G. 11

ABNORMALITY SCORE CALCULATION APPARATUS, METHOD, AND MEDIUM

CROSS-REFERENCE TO RELATED APPLICATIONS

This application is based upon and claims the benefit of priority from Japanese Patent Application No. 2020-155587, filed Sep. 16, 2020; the entire contents of which are incorporated herein by reference.

FIELD

Embodiments described herein relate generally to an abnormality score calculation apparatus, a method, and a medium.

BACKGROUND

In the manufacturing industry, detecting product defects or failures in manufacturing devices at an early stage and taking countermeasures lead to improvement of yield and thus take on great importance. For this reason, efforts are being made to acquire manufacturing data in the manufacturing process of products, visualize the data, detect abnormalities in products and manufacturing devices, and estimate causes of the abnormalities.

Detection of an abnormality and estimation of a cause of the abnormality use various types of data such as data concerning products such as product dimensions and electrical characteristics, data concerning manufacturing conditions such as materials used and a manufacturing device used, and data concerning a manufacturing device such as operating results of the manufacturing device. Therefore, data for use in detection of an abnormality and estimation of a cause of the abnormality include various types of data such as output values of a sensor and a flag indicating a manufacturing condition under which a product was manufactured. Furthermore, data for use in detection of an abnormality and estimation of a cause of the abnormality include data having various properties, such as continuous value data, discrete value data, and text data. Since the accuracy of continuous value data depends on the performance of a sensor that performs observation and a quality control index, the decimal point accuracy may differ for each piece of data. In addition, with the development of manufacturing IoT (Internet of Things) technology, various types of data concerning manufacturing becomes easily available and the number of items of manufacturing data increases. Along with this, the types and properties of data increase in various ways.

In detection of an abnormality and estimation of a cause of the abnormality, various types of processing are performed according to the type of data. In general, statistical processing is often used for data concerning products and data concerning manufacturing conditions. However, a method of manually analyzing a huge amount of data places a significant burden on an operator. Thus, such a method is extremely difficult. Therefore, in recent years, an attempt has been widely made to aggregate data for each manufacturing device or for each sensor installed in a manufacturing device, etc., to statistically process obtained data concerning a calculator, and to aggregate and analyze the results of the statistical processing.

For example, for the purpose of predicting a failure in a manufacturing device, a method of detecting a particular change point by performing a time series analysis using a value obtained by combining a plurality of indexes representing operation results of the manufacturing device has been proposed. This method uses a value obtained by combining a plurality of indexes for time series analysis, thereby making it possible to detect an abnormality that is difficult to judge if indexes are monitored individually. In addition, the above method uses data with similar properties such as operation results of a manufacturing device without using data with different properties for each sensor, such as sensor data (sensor output values). This offers the advantage that the above method can be implemented with a simple configuration without using specialized knowledge about a sensor configuration or sensing.

DETAILED DESCRIPTION

An abnormality score calculation apparatus according to an embodiment includes a processing circuit configured to:

acquire first data concerning a status of a product or a manufacturing process; calculate based on the first data an abnormality score for a respective one of a plurality of abnormality modes or for a respective one of a plurality of pieces of the first data of various types; and convert a scale of a respective one of a plurality of abnormality scores including the abnormality score in such a manner that the abnormality scores become substantially equal in occurrence degree.

Hereinafter, an abnormality score calculation apparatus, a method, and a medium will be described in detail with reference to the drawings. In the description below, structural elements having substantially the same functions will be denoted by the same reference symbols, and a repetitive description of such elements will be given only where necessary.

Figure 1:
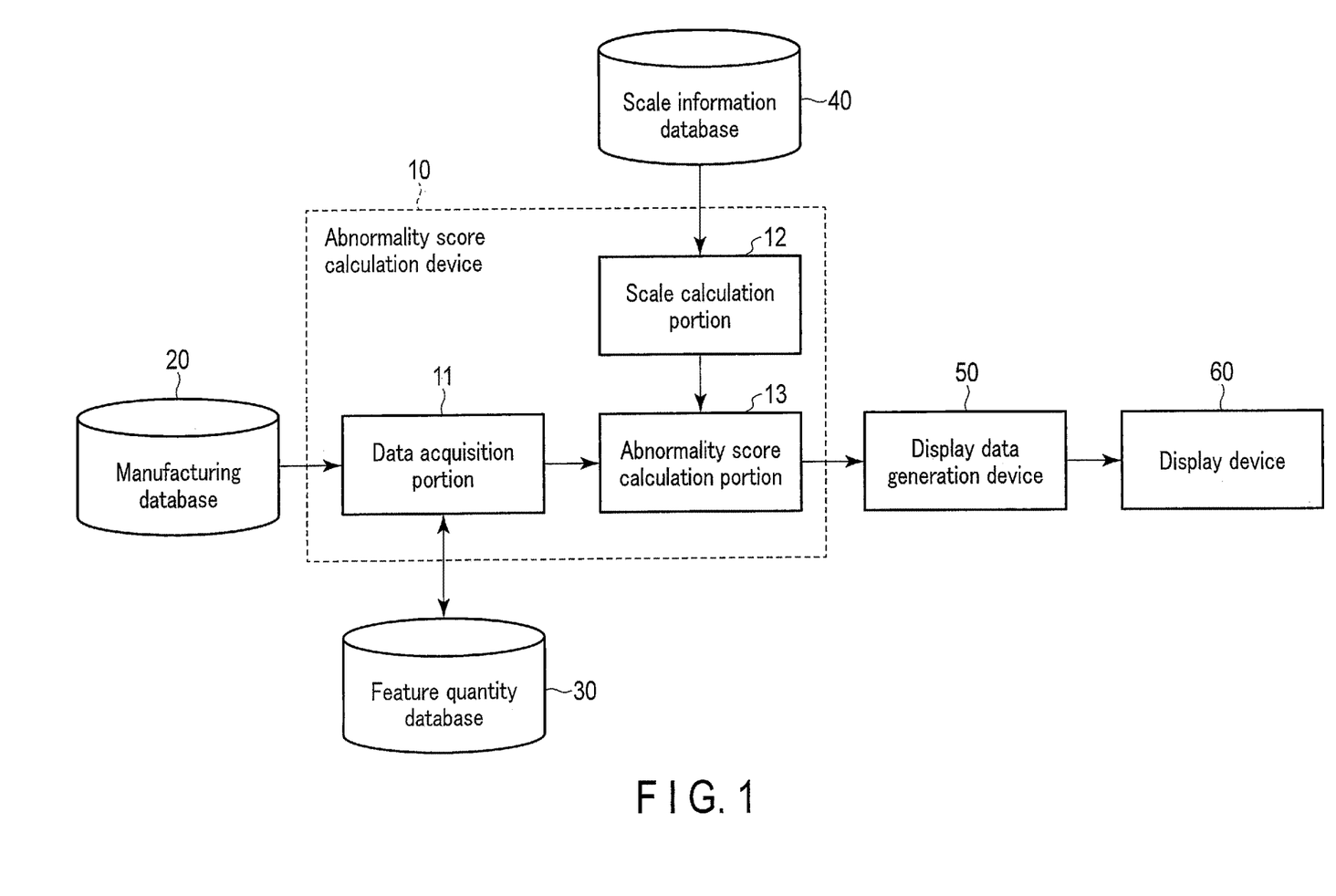
FIG. 1 is a diagram showing one example of a configuration of a system including an abnormality score calculation apparatus according to a present embodiment and peripheral devices of the abnormality score calculation apparatus.

FIG. 1 is a diagram showing a configuration of a system including an abnormality score calculation apparatus 10 according to the present embodiment and peripheral devices thereof. The abnormality score calculation apparatus 10 is connected to a manufacturing database 20, a feature quantity database 30, a scale information database 40, a display data generation device 50, and a display device 60 via a network. Examples of the network include a LAN (Local Area Network). It does not matter whether connection to a network is a wired connection or wireless connection. A line to be connected is not limited to a LAN. Connection may be made to a public communication line such as the Internet.

The manufacturing database 20 records data concerning a status of a product or a manufacturing process (hereinafter, referred to as manufacturing data pieces). The manufacturing data pieces include various types of data such as a continuous value, an integer value, category data, etc. The manufacturing data pieces include, for example, a sensor value acquired from a sensor installed in a product or a manufacturing device, a defective rate, etc.

In the manufacturing database 20, along with the manufacturing data pieces, an ID for identifying each product, an identification number of a manufacturing device, an identification number of a sensor, a time stamp indicating a date of manufacture, a unit of manufacturing management indicating products were manufactured under the same manufacturing conditions, a defective rate, manufacturing conditions, etc., are recorded for each manufacturing data piece. An example of the unit of manufacturing management is a lot. The following description assumes that the manufacturing database 20 is a general relational database management system (RDBMS). The manufacturing database 20 may be a NoSQL-type database or a database that takes a knowledge structure such as XML, etc. Data recorded in the manufacturing database 20 may be a file in a CSV format, a Json format, etc., and may be Raw data to be output from a manufacturing device.

Figure 2:
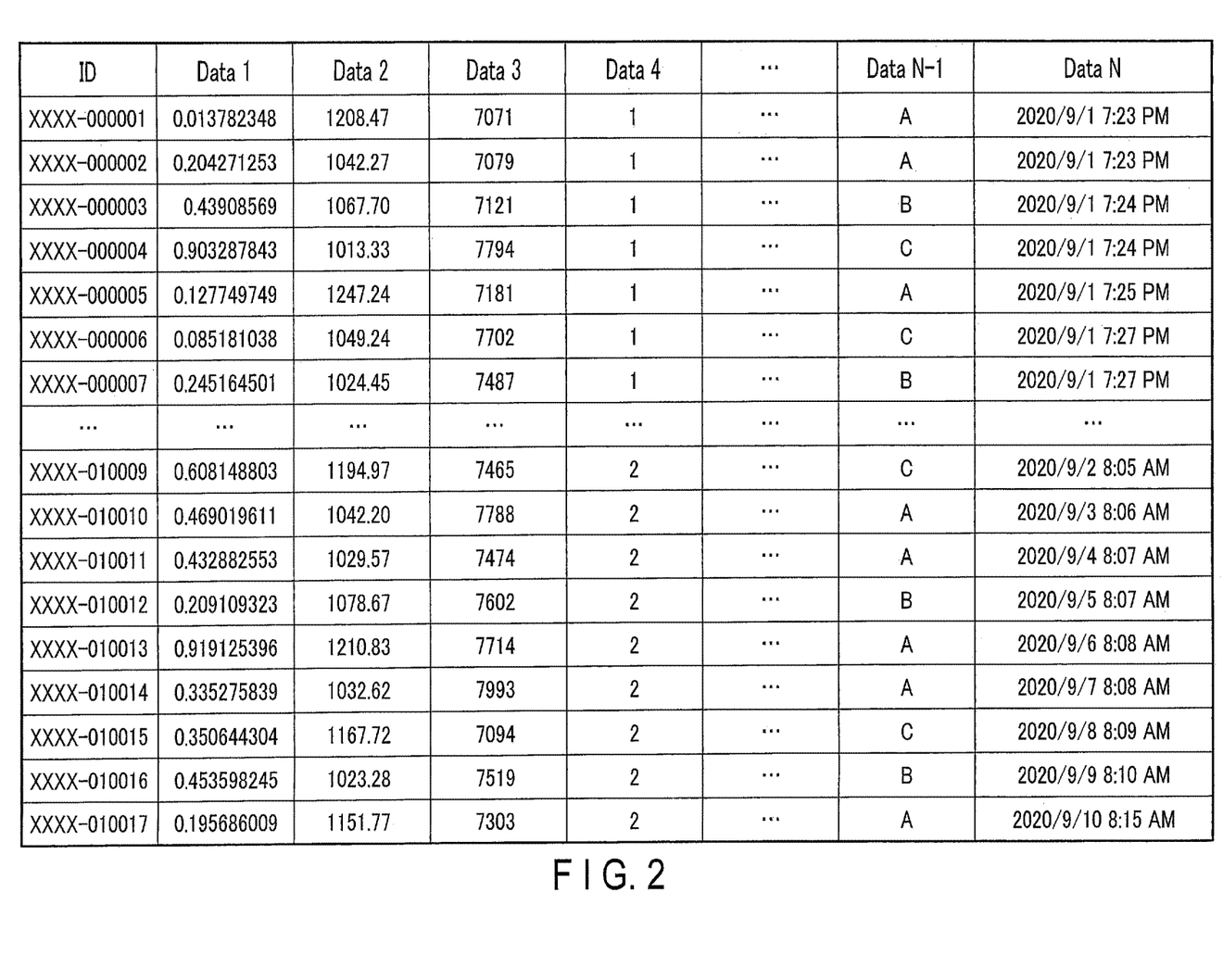
FIG. 2 is a diagram showing one example of data stored in a manufacturing database according to the present embodiment.

FIG. 2 is a diagram showing one example of data recorded in the manufacturing database 20. In FIG. 2, data in the column of "Data 1" represents manufacturing data pieces acquired from a manufacturing device assigned the identification number of "1", data in the column of "Data 2" represents manufacturing data pieces acquired from a manufacturing device assigned the identification number of "2", and data in the column of "Data 3" represents manufacturing data pieces acquired from a manufacturing device assigned the identification number of "3". As shown in FIG. 2, the manufacturing data piece may be a decimal having a large number of digits or a small number of digits, or may be an integer value. Data in the column of "Data 4" represents a unit of manufacturing management. The unit of manufacturing management may be an integer or category data. Data in the column of "Data N−1" represents category data. Examples of the category data include manufacturing conditions. Data in the column of "Data N" represents a time stamp. Data in the column of "ID" represents an ID of a product. Data in the column of "Data 1" may be a measurement value of a sensor assigned the identification number of "1". In addition to data shown in FIG. 2, manufacturing conditions, a defective rate, etc. may be recorded in the manufacturing database 20.

The feature quantity database 30 records a feature quantity of a manufacturing data piece. The feature quantity is obtained by converting a feature of a manufacturing data piece into a number. The feature quantity will be described later. Just as with the manufacturing database 20, the feature quantity database 30 may be a relational database management system (RDBMS), an NoSQL-type database, or a database that takes a knowledge structure, such as an XML, etc. Data recorded in the feature quantity database 30 may be a file in a CSV format, a Json format, etc.

In the scale information database 40, scale calculation information is recorded. The scale calculation information includes a past abnormality score. The abnormality score is a numerical value indicative of a degree of abnormality (a degree of change) in manufacturing data pieces. The abnormality score will be described later.

The abnormality score calculation apparatus 10 acquires the first data from the manufacturing database 20. The first data includes manufacturing data pieces. The abnormality score calculation apparatus 10 calculates a plurality of abnormality scores based on the acquired first data. The abnormality score is a value indicative of a degree of change in the first data. The abnormality score calculation apparatus 10 acquires scale calculation information from the scale information database 40, and based on the scale calculation information, converts the scale of each of the abnormality scores in such a manner that they become substantially equal in occurrence degree. The abnormality score calculation apparatus 10 outputs the scale-converted abnormality scores to the display data generation device 50. Applying the scale conversion to respective abnormality scores to make them substantially equal in occurrence degree includes conversion of an abnormality score into a value predicated on a probability of occurrence and normalization of an abnormality score. The degree of occurrence of an abnormality score may also be referred to as rarity of occurrence of an abnormality score.

Next, a configuration of the abnormality score calculation apparatus 10 will be described. The abnormality score calculation apparatus 10 includes a processing circuit that controls the entire abnormality score calculation apparatus 10, and a storage medium (memory). The processing circuit is a processor that executes functions of the data acquisition unit 11, the scale calculation unit 12, and the abnormality score calculation unit 13 by invoking and executing a program within the storage medium. The processing circuit is composed of an integrated circuit including a CPU (Central Processing Unit), an ASIC (Application Specific Integrated Circuit), an FPGA (Field Programmable Gate Array), etc. The processor may be composed of a single integrated circuit or a plurality of integrated circuits.

The storage medium stores processing programs for use in the processor as well as parameters, tables, etc., for use in operations in the processor. The storage medium is a storage device such as a Hard Disk Drive (HDD), a Solid State Drive (SSD), or an integrated circuit, which stores various types of information. Other than an HDD, an SSD, etc., the storage medium may be a portable storage medium such as a Compact Disc (CD), a Digital Versatile Disc (DVD), a flash memory, etc., or may be a driving device that reads and writes various types of information to and from, e.g., a semiconductor memory device such as a flash memory, a Random Access Memory (RAM), etc.

Each of the functions of the data acquisition unit 11, the scale calculation unit 12, and the abnormality score calculation unit 13 may be implemented by a single processing circuit. Alternatively, a processing circuit may be configured by combining a plurality of independent processors together, and each of the functions may be implemented by each of the processors executing a program. Each of the functions of the data acquisition unit 11, the scale calculation unit 12, and the abnormality score calculation unit 13 may be implemented in an individual hardware circuit.

The data acquisition unit 11 acquires the first data from the manufacturing database 20. The first data includes manufacturing data pieces. The manufacturing data pieces are mainly numerical data such as a continuous value, an integer value, etc. In the case of a manufacturing data piece being category data, the data acquisition unit 11 converts the category data into numerical data and acquires it. In this case, the data acquisition unit 11 converts category data into numerical data by taking an approach of, for example, making conversion into a numerical value corresponding to each category. Examples of the approach of making conversion into a numerical value corresponding to each category include label conversion, frequency conversion, etc.

The data acquisition unit 11 acquires, along with the first data, an ID, a time stamp, and a unit of manufacturing management, etc. of each manufacturing data piece, from the manufacturing database 20. However, if a manufacturing data piece such as a CSV format is acquired as the first data, an ID, a time stamp, and a unit of manufacturing management of the manufacturing data piece may not be recorded in the manufacturing database 20. In this case, the data acquisition unit 11 assigns a serial number, etc., to each manufacturing data piece of the first data.

Based on the first data, the data acquisition unit 11 further acquires two pieces of sub-data (first sub-data and second sub-data) on a predetermined condition. For example, the data acquisition unit 11 acquires the first sub-data and the second sub-data from the first data based on a data range set for each piece of sub-data. In the processing of calculating an abnormality score, the first sub-data and the second sub-data are used for the processing step of calculating an abnormality score of the first sub-data or the second sub-data by comparing them by a statistical approach, for example. The data range of the first sub-data and the second sub-data corresponds to a window size of a time-series analysis.

The data range of the sub-data is set to a range in accordance with the type of abnormality desired to be analyzed. This enables an analysis suitable for the type of abnormality. For example, depending on the type of abnormality, changes in data include a change over a short period and a change over a long period. In the case where a short-term change in data is desired to be analyzed, a short period is set to a data range. In the case where a medium-to long-term change in data is desired to be analyzed, a long period is set to a data range. In the case where an analysis-target period (comparison-target period) is determined, this period may be set to a data range.

For example, in the case where a given ID is set to a data range of sub-data, by referring to IDs, the data acquisition unit 11 acquires, as data of the sub-data concerned, data corresponding to the set ID from among the manufacturing data pieces included in the first data. Furthermore, for example, in the case where a given period is set to a range of data to be acquired, by referring to time stamps, the data acquisition unit 11 acquires, as data of the sub-data concerned, data included in the given period from among the manufacturing data pieces included in the first data. For example, the data acquisition unit 11 acquires data included in a first period, as data of the first sub-data, and acquires data included in the second period different from the first period, as data of the second sub-data. In the case where a given unit of manufacturing management is set to a range of data to be acquired, by referring to a units of manufacturing management, the data acquisition unit 11 acquires, as data of the sub-data concerned, data in the given unit of manufacturing management from among the manufacturing data pieces included in the first data.

The manufacturing data pieces included in the first sub-data and the manufacturing data pieces included in the second sub-data may overlap. The number of pieces of data included in the first sub-data may differ from the number of pieces of data included in the second sub-data. It is only required that the manufacturing data pieces included in the first sub-data and the manufacturing data pieces included in the second sub-data do not match perfectly.

Figure 3:
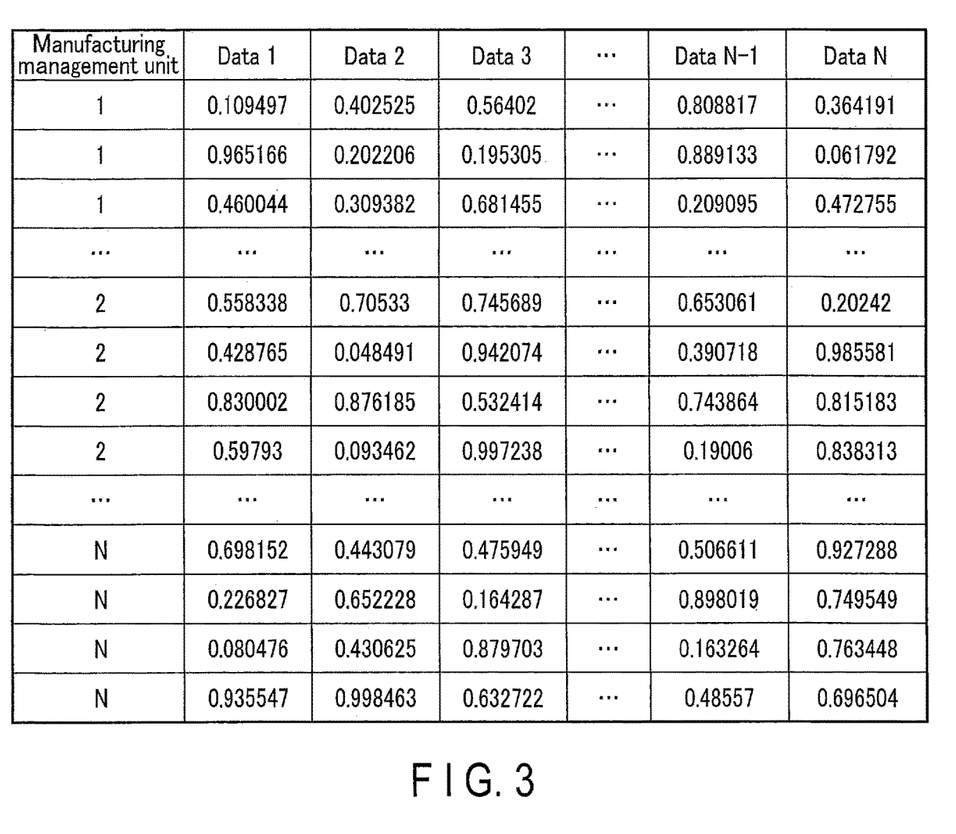
FIG. 3 is a diagram showing one example of first data acquired by an abnormality score calculation apparatus according to the present embodiment.

In the example described in the present embodiment, a manufacturing data piece, an identification number of a manufacturing device, and a unit of manufacturing management of each manufacturing data piece are acquired, and the unit of manufacturing management is set to a data range of sub-data. FIG. 3 is a diagram showing manufacturing data pieces and units of manufacturing management that are acquired by the data acquisition unit 11. In the table shown in FIG. 3, the horizontal axis (the column of the first data) represents identification numbers of manufacturing devices, whereas the vertical axis represents units of manufacturing management. For example, in the case where a unit of manufacturing management of "1" is set to a data range of the first sub-data (hereinafter, referred to as the first range), and a unit of manufacturing management of "2" is set to a data range of the second sub-data (hereinafter, referred to as the second range), the data acquisition unit 11 acquires, as the first sub-data, all manufacturing data pieces having a unit of manufacturing management of "1", from among the manufacturing data pieces included in the first data. The data acquisition unit 11 acquires, as the second sub-data, all manufacturing data pieces exhibiting a unit of manufacturing management of "2", from among the manufacturing data pieces included in the first data.

Furthermore, the data acquisition unit 11 acquires feature quantities of manufacturing data pieces included in the first data. The feature quantity is obtained by converting a feature of manufacturing data pieces included in the first data into a number. The feature quantity is calculated for each column of the first data based on each manufacturing data piece included in the first data. The feature quantity is calculated for each piece of sub-data based on each manufacturing data piece included in the first data. The feature quantity corresponds to fundamental statistics such as an average, a variance, a median, and a mode, a quantile, or the number of pieces of data. The feature quantity may be a variance, a standard deviation, or the like. The feature quantity may be intermediate generation data generated at the time of calculating the abnormality score. The feature quantity may be a vector sampled to reduce the volume of data, a probability density function, or a deep feature quantity. The feature quantity may be a vector obtained by dimensionally compressing the numerical values, etc., described above.

Figure 4:
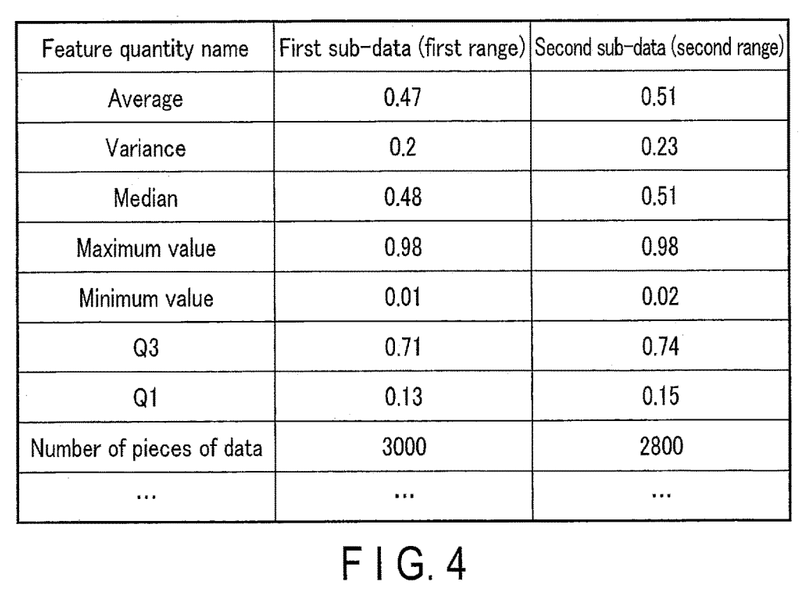
FIG. 4 is a diagram showing one example of feature quantities acquired by the abnormality score calculation apparatus according to the present embodiment.

The data acquisition unit 11 acquires the feature quantity of each of the first sub-data and the second sub-data from the feature quantity database 30. If no feature quantity is present in the feature quantity database 30, the data acquisition unit 11 calculates a feature quantity using the first data. FIG. 4 is a diagram showing one example of feature quantities. A calculated feature quantity is stored in the feature quantity database 30 and used for the processing of calculating an abnormality score.

In the present embodiment, an abnormality score is calculated using feature quantities. This reduces a time required for the processing regarding acquisition of data used for the calculation of an abnormality score or calculation of an abnormality score as compared to the case in which an abnormality score is calculated from the first data without using feature quantities.

Next, the abnormality score calculation unit 13 will be described. The abnormality score calculation unit 13 includes a first processing unit and a second processing unit. The first processing unit executes the processing of calculating a plurality of abnormality scores based on the first data. The second processing unit executes the processing of converting the calculated abnormality score, using scale calculation information received from the scale calculation unit 12.

The first processing unit of the abnormality score calculation unit 13 calculates an abnormality score for each of the abnormality modes of two or more types. Alternatively, the abnormality score calculation unit 13 calculates an abnormality score for each of the manufacturing data pieces of two or more types.

The abnormality mode represents a type of a parameter for use in calculation of an abnormality score. In the present embodiment, the abnormality mode represents a type of change (variation) between the first range and the second range. Examples of the abnormality mode include an average mode, a variation mode, and a distributed shape mode. The average mode is used in the case where there is a significant difference in average value between the first sub-data and the second sub-data. The variation mode is used in the case where, for example, the first sub-data and the second sub-data significantly differ in variance. The distributed shape mode is a mode for capturing a change in a distributed shape. Other than these, a mode indicating a change between the number of abnormalities included in the first sub-data and the number of abnormalities included in the second sub-data may be used as the abnormality mode. In this case, the number of abnormalities included in each piece of sub-data is calculated in advance by threshold value determination, etc.

The abnormality score calculation unit 13 may calculate a plurality of abnormality scores for the same type of change. That is, the abnormality score calculation unit 13 may calculate a plurality of types of abnormality scores for a single abnormality mode. In this case, in a single abnormality mode, the sensitivity with respect to a change is varied to respectively calculate abnormality scores for a plurality of different sensitivities. For example, in the case where both an average change and an outlier are present in the average mode, an abnormality score regarding a change in an average value between the first sub-data and the second sub-data and an abnormality score regarding a rigid change in median between the first sub-data and the second sub-data are used.

In the present embodiment, an example in which an abnormality score is calculated for each of the two or more types of abnormality modes will be described. By calculating abnormality scores for a plurality of abnormality modes, changes in data can be grasped from various angles.

An abnormality score is calculated by an algorithm in accordance with an abnormality mode. Examples of the abnormality score include a difference or ratio in feature quantity between the first range and the second range. For example, in the case where the abnormality mode is the average mode, the abnormality score calculation unit 13 calculates a difference or ratio in average between the first range and the second range as an abnormality score. For example, in the case where the abnormality score is a difference in average between the first range and the second range, an abnormality score $S_\mu$ is determined using the equation (1). Here, $\mu 1$ represents an average value of the first range and $\mu 2$ represents an average value of the second range. Alternatively, the abnormality score Sp may be calculated using the equation (2) in such a manner that the abnormality score takes on a positive value. Instead of the average value, the abnormality score may be calculated using a feature quantity by which a change in average such as a median can be captured.

[Equation 1]

$$S_\lambda = \mu 1 - \mu 2 \qquad (1)$$

[Equation 2]

$$S_\mu^2 = (\mu 1 - \mu 2)^2 \qquad (2)$$

In the case in which the abnormality mode is other than the average mode, the abnormality score calculation unit 13 calculates an abnormality score by applying a feature quantity or an algorithm suitable for the abnormality mode. For example, in the case where the abnormality mode is the variation mode, the abnormality score calculation unit 13 calculates an abnormality score by using a standard deviation of the first range and a standard deviation of the second range as feature quantities.

It is also possible to calculate the abnormality score without using a feature quantity. In this case, for example, the abnormality score is calculated using a distance or similarity between data pieces, instead of a difference or ratio therebetween. For example, the Kullback-Leibler information amount or the Jensen-Shannon information amount between the quantiles of the first range and the second range may be calculated as the abnormality score. Other than the above, a cosine distance between the first range and the second range, a correlation coefficient, etc., may be used as the abnormality score.

It is also possible to calculate the abnormality score without using the sub-data. For example, the abnormality score can be calculated using an abnormality detection algorithm. In this case, the abnormality detection algorithm such as threshold processing or One Class SVM is applied to each column of the first data with respect to the manufacturing data pieces included in the first data, and a ratio of, e.g., the number of abnormalities obtained from the result of the abnormality detection algorithm is set to the abnormality score. Specifically, for example, a ratio of the number of detected cases to the total number of data pieces to which the abnormality detection algorithm is applied (estimated abnormality occurrence rate) is calculated as the abnormality score. In the abnormality detection algorithm, the sensitivity of abnormality detection may change depending on a parameter. In such a case, a plurality of abnormality scores may be calculated by changing a parameter.

Next, the scale calculation unit 12 will be described. The scale calculation unit 12 acquires scale calculation information from the scale information database 40. The scale calculation information includes abnormality scores calculated in the past. The scale calculation unit 12 statistically models a distribution of past abnormality scores by using a statistical modeling method. At this time, the distribution of past abnormality scores is statistically modeled for each abnormality mode with respect to each column of the first data. As a statistical model, for example, a statistical distribution such as a gamma distribution, a chi-square distribution, a normal distribution, etc. is used. The scale calculation unit 12 outputs the statistically modeled distribution of abnormality scores to the abnormality score calculation unit 13 as scale calculation information.

Next, the processing by the second processing unit of the abnormality score calculation unit 13 will be described. First, the abnormality score calculation unit 13 acquires the statistically modeled distribution of abnormality scores as scale calculation information from the scale calculation unit 12. Next, based on the scale calculation information, the abnormality score calculation unit 13 converts the scale of each of the abnormality scores in such a manner as to make them substantially equal in degree of rarity of occurrence. Specifically, the abnormality score calculation unit 13 fits a statistical model of a distribution of past abnormality scores to a distribution of abnormality scores, and calculates probabilities corresponding to abnormality scores in the fitted statistical model as scale-converted abnormality scores. The scale-converted abnormality scores are output to the display data generation device 50. By statistically modeling a distribution of abnormality scores, a plurality of abnormality scores different in distribution can be handled as probability values based on a frequency of occurrence. This makes it easy to make a comparison in abnormality score between different columns or between different abnormality modes.

Figure 7:
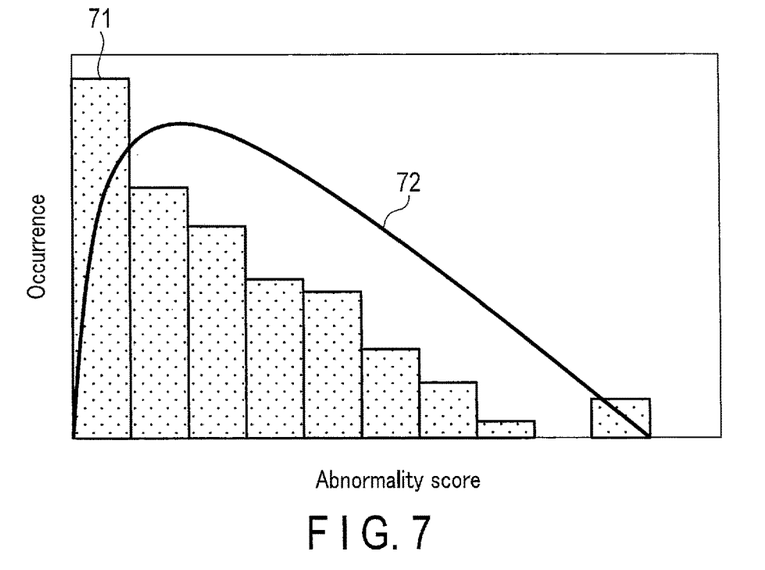
FIG. 7 is a diagram for illustrating one example of a method of converting a scale of abnormality scores in the scale conversion processing performed by the abnormality score calculation apparatus according to the present embodiment.

One example of a method of converting the scale of an abnormality score by using a statistical modeling method will be described with reference to FIGS. 7 and 8. FIG. 7 is a diagram for illustrating a method of statistically modeling a distribution of past abnormality scores by the scale calculation unit 12. In FIG. 7, a gamma distribution is used as a statistical model. The gamma distribution is used when statistical modeling is performed on values that take on positive continuous values by estimating two parameters by maximum-likelihood estimation. In FIG. 7, the horizontal axis represents values of abnormality scores. In FIG. 7, the vertical axis represents frequencies of abnormality scores. FIG. 7 shows a histogram 71 showing a distribution of past abnormality scores. Furthermore, FIG. 7 shows a statistical model 72 that is statistically modeled by the scale calculation unit 12 based on a distribution of past abnormality scores. An abnormality score described herein increases in value as a manufacturing data piece becomes more abnormal.

Figure 8:
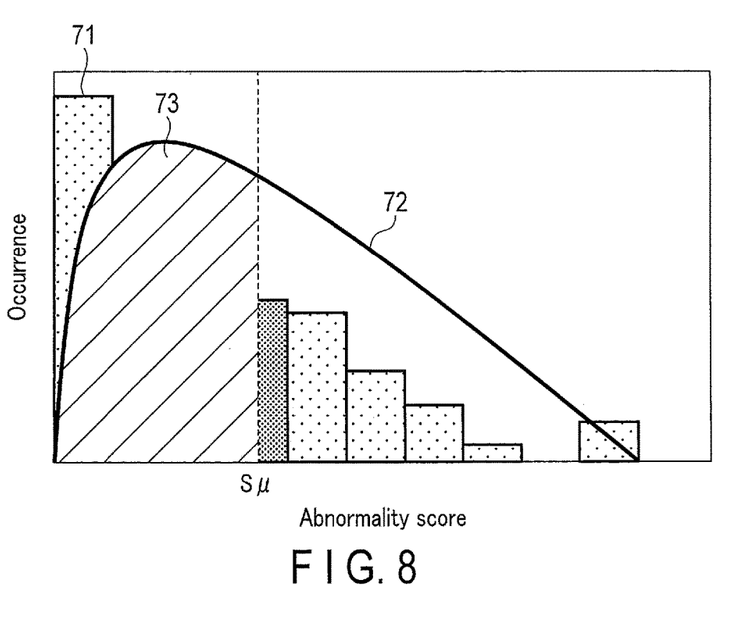
FIG. 8 is a diagram for illustrating another example of a method of converting the scale of abnormality scores in the scale conversion processing performed by the abnormality score calculation apparatus according to the present embodiment.

FIG. 8 is a diagram for illustrating the processing of converting the scale of an abnormality score using a statistical model. In this example, by using the abnormality score Sp calculated by the first processing unit of the abnormality score calculation unit 13 and the statistical model 72, the abnormality score calculation unit 13 first calculates a lower probability based on a percentage point that is set to the abnormality score Sp. The lower probability corresponds to an area included in a shaded area 73 in FIG. 8. Next, the abnormality score calculation unit 13 outputs the calculated lower probability as a scale-converted abnormality score to the display data generation device 50. The scale-converted abnormality score takes on a numerical value of 0 or more and 1 or less. The scale-converted abnormality score indicates that the probability of occurrence decreases as the numerical value becomes closer to 1.

Regarding an abnormality score whose value becomes smaller as a manufacturing data piece becomes more abnormal, the abnormality score calculation unit 13 calculates an upper probability based on the percentage point set to the abnormality score Sp, and sets the calculated upper probability to a scale-converted abnormality score.

The scale of an abnormality score may be converted without using the statistical modeling method. For example, the scale of an abnormality score may be converted using a method called data normalization or a method called data standardization. In the case of converting a value of an abnormality score using data normalization, the scale calculation unit 12 acquires a past abnormality score as scale calculation information from the scale information database 40, and extracts the maximum value Xmax and the minimum value Xmin of the abnormality score based on the scale calculation information. The second processing unit of the abnormality score calculation unit 13 acquires the maximum value Xmax and the minimum value Xmin of the abnormality score as scale calculation information. The abnormality score calculation unit 13 normalizes the abnormality score by using the equation (3). Herein, Xnorm represents a normalized abnormality score, Xmax represents the maximum value of the abnormality score, Xmin represents the minimum value of the abnormality score, and X represents the abnormality score to which normalization is applied.

[Equation 3]

$$x_{norm} = \frac{x - x_{min}}{x_{max} - x_{min}} \quad (3)$$

In the case where a manufacturing management criteria are predetermined for measurement values of manufacturing data pieces, the scale of an abnormality score may be converted by using the manufacturing management criteria. The manufacturing management criteria include the upper limit value and the lower limit value of measurement values of the manufacturing data pieces. A product corresponding to a measurement value between or equal to the lower limit value and the upper limit value is treated as a non-defective product. On the other hand, a product corresponding to a measurement value greater than the upper limit value or a measurement value smaller than the lower limit value is treated as a defective product. In this case, based on the upper and lower limit values, the scale of the abnormality score is converted in such a manner that the maximum possible change within the manufacturing management criteria corresponds to the maximum value of the abnormality score.

For example, the scale calculation unit 12 calculates a range of values that the abnormality score can take when the measurement value changes within a range that satisfies the manufacturing management criteria, and determines the maximum value and the minimum value of the abnormality score. The scale calculation unit 12 outputs, as scale calculation information, the maximum value and the minimum value of the abnormality score to the abnormality score calculation unit 13. The second processing unit of the abnormality score calculation unit 13 converts the scale of the abnormality score by applying the maximum value and the minimum value of the abnormality score to the same formula as in the formula (3). In this way, by conforming a scale of the abnormality score to the manufacturing management criteria, a degree of abnormality of the abnormality score can be judged in light of the manufacturing management criteria.

In addition, the scale of an abnormality score may be converted to a numerical value predicated on the probability of occurrence of the abnormality score by using the manufacturing management criteria. In this case, first, the scale calculation unit 12 calculates the abnormality score based on a measurement value between or equal to the lower limit value and the upper limit value within the manufacturing management criteria, thereby estimating a range of values that the abnormality score can take in compliance with the manufacturing management criteria. Then, the maximum value (estimated value) of the abnormality score calculated based on a measurement value that satisfies the manufacturing management criteria is estimated based on the range of values that the abnormality score can take. Next, the scale calculation unit 12 generates a statistical model (scale conversion model) by fitting to the statistical model a distribution from which the abnormality score of a value larger than the maximum value is removed. At this time, the abnormality score that exhibits a measurement value between or equal to the lower limit value and the upper limit value within the manufacturing management criteria is converted (clipped) so as to take the maximum value within the range of values that the abnormality score can take. Specifically, after converting an abnormality score larger than the maximum value into the maximum value, the scale calculation unit 12 generates a statistical model using a distribution of the converted abnormality score. The second processing unit of the abnormality score calculation unit 13 converts the scale of the abnormality score using the generated statistical model. Even in this case, by calculating the scale of the abnormality score based on the manufacturing management criteria, a degree of abnormality of the abnormality score can be judged in light of the manufacturing management criteria.

The display data generation device 50 acquires the scale-converted abnormality score from the abnormality score calculation apparatus 10, and generates display data for displaying the scale-converted abnormality score. The display data generation device 50 outputs the generated display data to the display device 60.

The display device 60 acquires display data for displaying the scale-converted abnormality score from the display data generation device 50, and displays the acquired display data. Examples of the display device 60 include a liquid crystal display.

Figure 5:
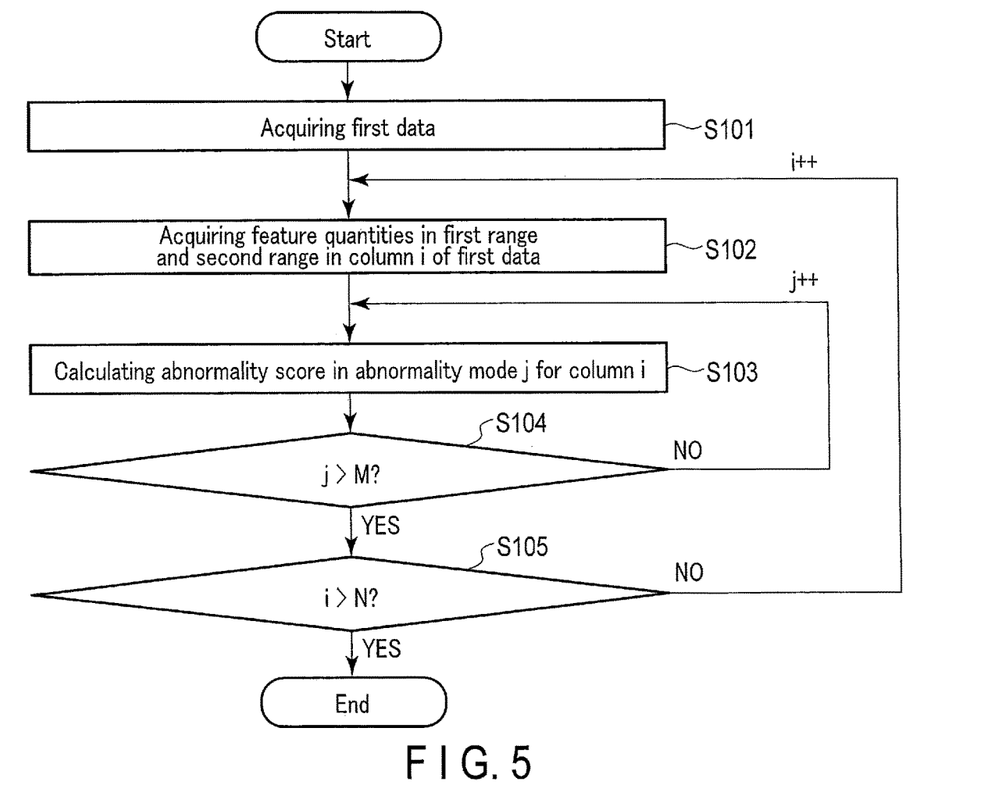
FIG. 5 is a flowchart showing an exemplary processing procedure of abnormality score calculation processing performed by the abnormality score calculation apparatus according to the present embodiment.

Next, the operation of processing executed by the abnormality score calculation apparatus 10 will be described. FIG. 5 is a flowchart showing one example of a processing procedure of abnormality score calculation processing. The abnormality score calculation processing is processing of acquiring data for calculating the abnormality score and calculating the abnormality score. The processing procedure in each instance of processing described below is merely an example, and each instance of processing can be appropriately changed where possible. Furthermore, with respect to the processing procedure described below, steps can be omitted, replaced, and added as appropriate according to the embodiment.

As shown in FIG. 5, first, the data acquisition unit 11 acquires the first data including manufacturing data pieces, and the unit of manufacturing management of each manufacturing data piece (step S101). Herein, the total number of columns of manufacturing data pieces is represented as N, and a column number of a manufacturing data piece is represented as i (1□i□N). For example, data in a column i is a manufacturing data piece acquired from a manufacturing device having the identification number of "1". Next, with respect to the column i of the first data, the data acquisition unit 11 calculates the feature quantity in the first range and the feature quantity in the second range by using the first sub-data including manufacturing data pieces in the first range and the second sub-data including manufacturing data pieces in the second range, and acquires the calculated feature quantities (step S102). Next, the abnormality score calculation unit 13 compares the feature quantity in the first range and the feature quantity in the second range in the column i of the first data, thereby calculating the abnormality score in an abnormality mode j (Step S103). Herein, the total number of abnormality modes is represented as M, and a serial number of an abnormality mode is represented as j (1□j□M). The abnormality score calculation unit 13 calculates M abnormality scores for the column i of the first data by repeating the processing at step S103 for all the abnormality modes (steps S103 and S104). Furthermore, the abnormality score calculation unit 13 calculates M abnormality scores for each of the N columns by repeating the processing at steps S102 to S104 for all the columns of the first data (steps S102 to S105).

Figure 6:
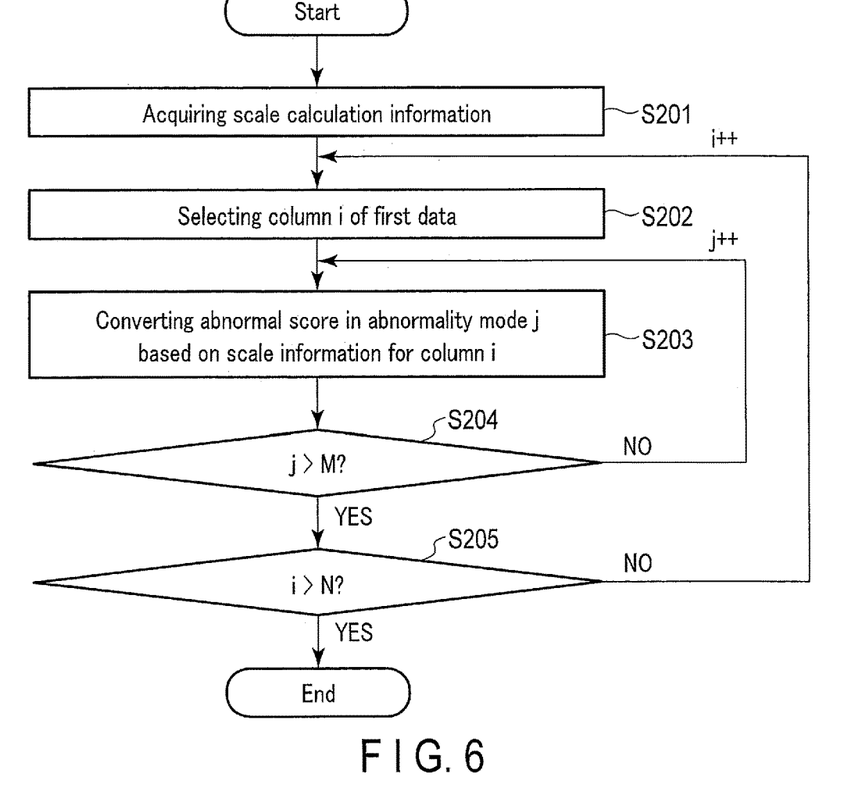
FIG. 6 is a flowchart showing an exemplary processing procedure of scale conversion processing performed by the abnormality score calculation apparatus according to the present embodiment.

FIG. 6 is a flowchart showing one example of a procedure of the scale conversion processing. The scale conversion processing is processing of acquiring scale calculation information for use in the scale conversion of the abnormality score and converting the scale of the abnormality score based on the scale calculation information.

As shown in FIG. 6, first, the scale calculation unit 12 acquires past abnormality scores as scale calculation information, and statistically models the abnormality score based on a degree of occurrence in the past (step S201). Next, the scale calculation unit 12 outputs, as scale calculation information, the statistical model of the abnormality score to the second processing unit of the abnormality score calculation unit 13. Next, the abnormality score calculation unit 13 selects the column i of the first data (step S202). Next, for the column i of the first data, the abnormality scale calculation unit 13 converts the abnormality score in the abnormality mode j based on the scale calculation information (step S203). The abnormality score calculation unit 13 converts the abnormality score for M abnormality modes in the column i of the first data by repeating the processing at step S203 for all the abnormality modes (steps S203 and S204). The abnormality score calculation unit 13 further converts each of the abnormality scores of the M abnormality modes for each of the N columns by repeating the processing at steps S202 to S204 for all the columns of the first data (steps S202 to S205). By this, the calculated abnormality scores are converted into substantially the same scale between the columns and between the abnormality modes based on the degree of past occurrence.

The scale-converted abnormality scores are output from the abnormality score calculation apparatus 10 to the display data generation device 50. The display data generation device 50 generates a display screen on which the scale-converted abnormality scores are displayed, and the display device 60 displays the display screen.

Figure 9:
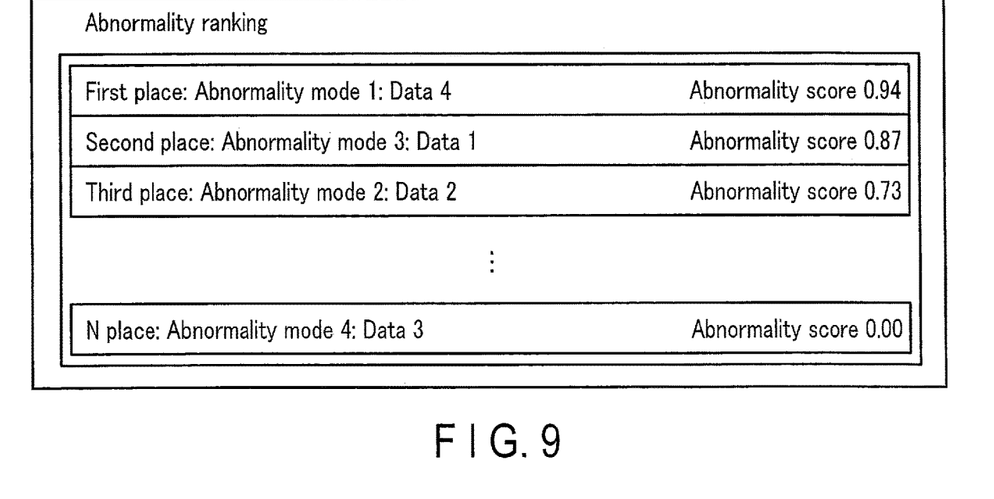
FIG. 9 is a diagram showing one example of a display screen configured to display abnormality scores calculated by the abnormality score calculation apparatus according to the present embodiment.

FIG. 9 is a diagram illustrating one example of a display screen displayed on the display device 60. On the display screen shown in FIG. 9, a plurality of scale converted abnormality scores are displayed in a ranking format in order of magnitude. On the display screen shown in FIG. 9, the plurality of scale-converted abnormality scores are displayed in descending order of value. The scale-converted abnormality score indicates that the probability of occurrence decreases as the numerical value is closer to 1. This indicates that an abnormality score displayed in a higher position has an abnormality with a smaller probability of occurrence. By checking the display screen, an operator can compare the abnormality scores between various abnormality modes and between various items (for example, manufacturing devices).

Figure 10:
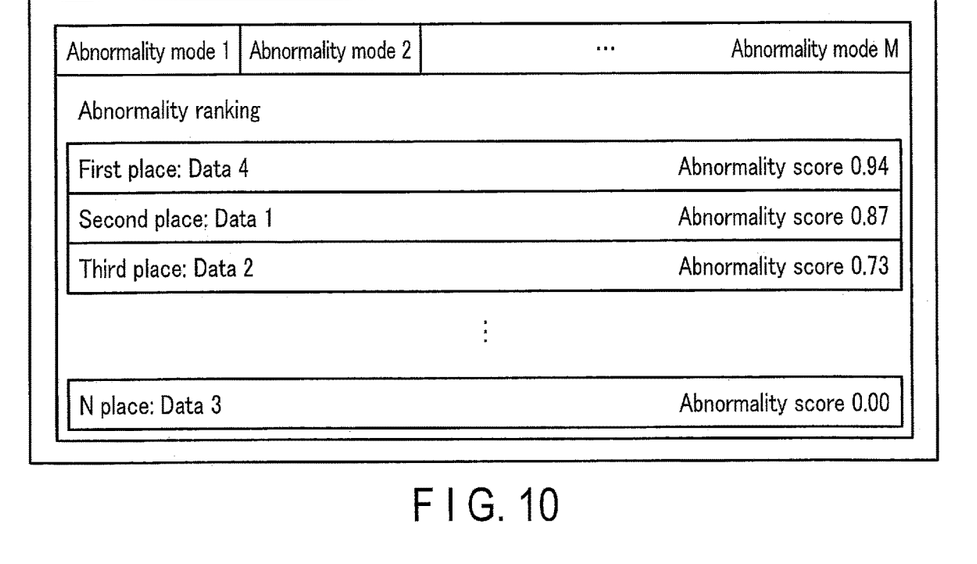
FIG. 10 is a diagram for illustrating another example of a method of converting the scale of abnormality scores in the scale conversion processing performed by the abnormality score calculation apparatus according to the present embodiment.

FIG. 10 is a diagram showing another example of the display screen displayed on the display device 60. On the display screen shown in FIG. 10, for each abnormality mode, the scale-converted abnormality scores are displayed in a ranking format in order of magnitude. By checking the display screen, the operator can compare the abnormality scores calculated in the same abnormality mode, between various items (for example, between various manufacturing devices).

Figure 11:
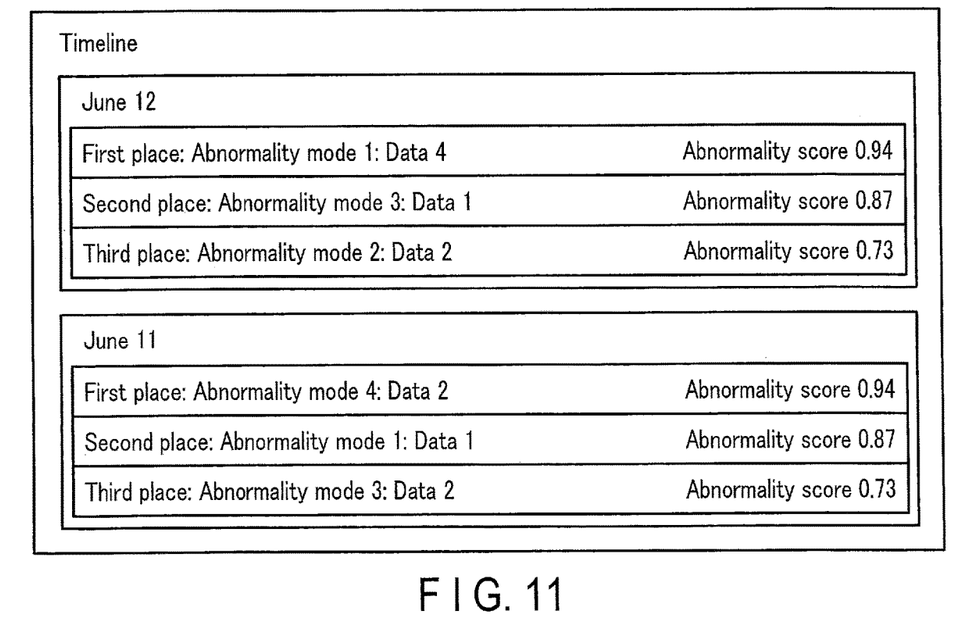
FIG. 11 is a diagram for illustrating yet another example of a method of converting the scale of abnormality scores in the scale conversion processing performed by the abnormality score calculation apparatus according to the present embodiment.

FIG. 11 is a diagram showing another example of the display screen displayed on the display device 60. On the display screen shown in FIG. 11, the scale-converted abnormality scores are displayed on the timeline in chronological order. On the display screen shown in FIG. 11, the top several abnormality scores are extracted in the order of magnitude of values and are displayed in a ranking format for each date on which the abnormality scores are calculated. By this, only data concerning an abnormality which should be checked is displayed. By checking the display screen, an operator can grasp the change over time in the abnormality score. Furthermore, only an abnormality score equal to or greater than a predetermined threshold value may be displayed for each date on which the abnormality score is calculated.

Hereinafter, the effect of the abnormality score calculation apparatus 10 according to the present embodiment will be described.

The abnormality score calculation apparatus 10 according to the present embodiment acquires the first data concerning a status of a product or a manufacturing process, and calculates based on the first data the abnormality score for each of the plurality of abnormality modes or calculates based on the first data the abnormality score for each of the plurality of items of the first data, and then converts the scale of each of the plurality of abnormality scores in such a manner as to make them substantially equal in degree of occurrence of an abnormality score.

The scale-converted abnormality scores are output from the abnormality score calculation apparatus 10 to the display data generation device 50. The display data generation device 50 generates a display screen on which the scale-converted abnormality scores are displayed, and the display device GO displays the display screen.

With the above configuration, according to the abnormality score calculation apparatus 10 according to the present embodiment, values concerning a plurality of abnormalities calculated based on various manufacturing data pieces obtained from a plurality of manufacturing devices and a plurality of sensors can be converted to a comparable form. Based on the converted values, an operator can intuitively determine in which manufacturing device or under what manufacturing conditions an abnormality has occurred. In addition, the operator can intuitively determine the degree of abnormality and what kind of abnormality has occurred. Furthermore, in a case in which a plurality of abnormalities occur at the same time, the operator can determine the priority of the abnormalities that have occurred, based on the values converted into a comparable form. In addition, the operator can immediately take appropriate measures by referring to past cases regarding similar abnormalities or abnormality handling manuals. Specifically, the burden of analyzing an abnormality can be reduced by calculating abnormality scores with substantially the same scale for the abnormalities in the manufacturing data pieces.

Furthermore, in the present embodiment, the abnormality scores can be calculated as manufacturing data pieces, using detection values (sensor data) of a plurality of sensors installed in the same manufacturing device. The operator can investigate the abnormality situation in detail by checking the abnormality scores calculated using data of a plurality of sensors installed in the same manufacturing device.

The abnormality score calculation apparatus 10 according to the present embodiment converts the scale of each abnormality score by converting each abnormality score into a numeric value predicated on a probability of occurrence of each abnormality score, based on a distribution of occurrence of each past abnormality score. For example, by converting an abnormality score into a numeric value predicated on a probability of occurrence by using the statistical model of a distribution of past abnormality scores, a plurality of abnormality scores different in distribution can be handled as probability values predicated on a frequency of occurrence. This makes it possible to make a comparison in abnormality score between different manufacturing devices or between different sensors or to make a comparison in abnormality score between different abnormality modes.

Furthermore, the abnormality score calculation apparatus 10 according to the present embodiment calculates the abnormality score by comparing the feature quantity in the first range with the feature quantity in the second range. Calculating an abnormality score using feature quantities enables reduction in a time required for the processing regarding acquisition of data at the time of the calculation of an abnormality score or calculation of an abnormality score as compared to the case in which an abnormality score is calculated from the first data without using feature quantities.

In the present embodiment, an example in which the display data generation device 50 is provided separately from the abnormality score calculation apparatus 10 has been described; however, the abnormality score calculation apparatus 10 may include the same function as the function of the display data generation device 50. In such a case, the abnormality score calculation apparatus 10 further includes a generation unit that acquires an abnormality score for which the scale was converted and generates display data for displaying the scale-converted abnormality data. The display data generation device 50 and the abnormality score calculation apparatus 10 including the generation unit may be called a visualization device.

According to the abnormality score calculation apparatus, the method, and the medium of at least one embodiment described above, by converting a scale of a respective one of a plurality of abnormality scores including an abnormality score in such a manner that the abnormality scores become substantially equal in occurrence degree, it is possible to convert the plurality of values concerning abnormalities calculated based on various manufacturing data pieces into a comparable form.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An abnormality score calculation apparatus comprising a processing circuit configured to:
   acquire first data concerning a status of a product or a manufacturing process;
   calculate based on the first data an abnormality score for a respective one of a plurality of abnormality modes or for a respective one of a plurality of pieces of the first data of various types; and
   convert a scale of a respective one of a plurality of abnormality scores including the abnormality score in such a manner that the abnormality scores become substantially equal in occurrence degree by converting the abnormality score into a numerical value predicated on a probability of occurrence of the abnormality score, based on a distribution of occurrence of past abnormality scores.

2. The apparatus according to claim 1, wherein the processing circuit is configured to acquire the first data in a first range and the first data in a second range, and calculate the abnormality scores by comparing the first data in the first range with the first data in the second range.

3. The apparatus according to claim 2, wherein:
   the first range corresponds to a first period; and
   the second range corresponds to a second period different from the first period.

4. The apparatus according to claim 2, wherein:
   the first range is a range determined based on a unit of manufacturing management of the product; and
   the second range is a range determined based on a unit of manufacturing management different from the unit of manufacturing management of the first range.

5. The apparatus according to claim 2, wherein the processing circuit is configured to calculate a feature quantity in the first range and output the calculated feature quantity.

6. The apparatus according to claim 2, wherein the processing circuit is configured to acquire a feature quantity in the first range and a feature quantity in the second range, and calculate the abnormality score by comparing the feature quantity in the first range with the feature quantity in the second range.

7. The apparatus according to claim 1, wherein the processing circuit is configured to fit a statistical model of a distribution of past abnormality scores to a distribution of the abnormality scores, and calculate a probability corresponding to the abnormality score in the fitted statistical model, as a scale-converted abnormality score.

8. The apparatus according to claim 1, wherein the processing circuit is configured to convert the scale of the abnormality score by converting the abnormality score into a numerical value predicated on a probability of occurrence of the abnormality score, based on a manufacturing management criterion of the first data.

9. The apparatus according to claim 1, wherein the processing circuit is configured to acquire a scale-converted abnormality score, and generate display data for displaying the scale-converted abnormality score.

10. The apparatus according to claim 1, wherein the first data includes a detection value of a sensor installed in a manufacturing device.

11. The apparatus according to claim 1, wherein the processing circuit is configured to generate the distribution of occurrence of past abnormality scores using a measurement value obtained by removing an outlier from a past measurement value.

12. The apparatus according to claim 11, wherein the outlier is out of a range of management values or standard values.

13. An abnormality score calculation method comprising:
   acquiring first data concerning a status of a product or a manufacturing process;
   calculating based on the first data an abnormality score for a respective one of a plurality of abnormality modes or for a respective one of a plurality of pieces of the first data of different types; and
   converting a scale of a respective one of a plurality of abnormality scores including the abnormality score in such a manner that the abnormality scores become substantially equal in occurrence degree by converting the abnormality score into a numerical value predicated on a probability of occurrence of the abnormality score, based on a distribution of occurrence of past abnormality scores.

14. A non-transitory computer readable medium including computer executable instructions, wherein the instructions, when executed by a processor, cause the processor to perform a method comprising:
   acquiring first data concerning a status of a product or a manufacturing process;
   calculating based on the first data an abnormality score for a respective one of a plurality of abnormality modes or for a respective one of a plurality of pieces of the first data of different types; and
   converting a scale of a respective one of a plurality of abnormality scores including the abnormality score in such a manner that the abnormality scores become substantially equal in occurrence degree by converting the abnormality score into a numerical value predicated on a probability of occurrence of the abnormality score, based on a distribution of occurrence of past abnormality scores.

* * * * *